(12) United States Patent
Rossi

(10) Patent No.: US 10,052,250 B2
(45) Date of Patent: Aug. 21, 2018

(54) OPENABLE HELMET OF NON-INVASIVE VENTILATION OF PATIENTS

(71) Applicant: INTERSURGICAL S.P.A., Mirandola (Modena) (IT)

(72) Inventor: Paolo Rossi, Mirandola (IT)

(73) Assignee: INTERSURGICAL S.P.A., Mirandola (Modena) (IT)

( * ) Notice: Subject to any disclaimer, the term of this patent is extended or adjusted under 35 U.S.C. 154(b) by 397 days.

(21) Appl. No.: 13/889,026

(22) Filed: May 7, 2013

(65) Prior Publication Data

US 2014/0331999 A1    Nov. 13, 2014

(51) Int. Cl.
| | | |
|---|---|---|
| A61G 10/04 | (2006.01) | |
| A61M 16/06 | (2006.01) | |
| A61M 16/20 | (2006.01) | |

(52) U.S. Cl.
CPC ......... *A61G 10/04* (2013.01); *A61M 16/0627* (2014.02); *A61M 16/208* (2013.01)

(58) Field of Classification Search
CPC .......... A61M 16/06257; A61M 16/208; A61M 16/0057; A61M 16/0816; A61M 16/0875; A61M 16/06; A61M 39/1011; A61M 2039/1027; A61G 10/04; A62B 17/04; A62B 18/00; A62B 18/003; A62B 18/025; A62B 18/04; A62B 18/084

USPC ............ 128/201.23–201.29, 202.19, 202.27, 128/203.12, 205.26; 2/424, 171.3
See application file for complete search history.

(56) References Cited

U.S. PATENT DOCUMENTS

| | | | |
|---|---|---|---|
| 3,559,209 A | 2/1971 | Vail | |
| 3,994,635 A | 11/1976 | McCullough | |
| 6,854,459 B1* | 2/2005 | Cox | 128/201.23 |
| 2006/0100374 A1* | 5/2006 | Hamada et al. | 525/132 |
| 2006/0137686 A1* | 6/2006 | Macris | 128/201.22 |
| 2006/0264911 A1 | 11/2006 | Nelson | |
| 2008/0264413 A1* | 10/2008 | Doherty et al. | 128/202.27 |
| 2008/0302361 A1 | 12/2008 | Snow et al. | |
| 2011/0073109 A1 | 3/2011 | Mayer et al. | |

* cited by examiner

*Primary Examiner* — Todd J Scherbel
*Assistant Examiner* — Elliot S Ruddie
(74) *Attorney, Agent, or Firm* — Volpe and Koenig, P.C.

(57) ABSTRACT

A helmet (10) for non-invasive ventilation of patients comprising:
  a container body (20) in which there can be housed the head of a patient, provided with at least one optically transparent portion and with an open end to which a first rigid ring (21) is fixed;
  an elastically yieldable collar (30) which can be sealingly coupled to the neck of the patient and fixed to a second rigid ring (31) can be sealingly removably associated to said first rigid ring (21),
whose distinguishing characteristic consists in comprising a bayonet-like coupling means adapted to removably couple the first and the second rigid ring with respect to each other (21,31).

10 Claims, 9 Drawing Sheets

OPENABLE HELMET OF NON-INVASIVE VENTILATION OF PATIENTS

FIELD OF THE INVENTION

The present invention regards a helmet for non-invasive ventilation of patients.

More in particular, the invention regards a helmet for the artificial breathing of patients without using masks or tracheal tubes.

PRIOR ART

As known, generally used for non-invasive ventilation of patients are helmets which are generally made up of a substantially cylindrical container body to which there are connected air and oxygen inlet and outlet ports and which is provided with a collar made up of a thin membrane made of elastically yieldable plastic material coupled to the neck of the patient to provide sealing.

Such collar is made up of an extremely flexible film which adheres to the skin of the patient without exerting pressure.

Such helmets are used in oxygen therapy and for ventilating patients with continuous positive pressure, the so-called CPAP and NIV.

However, the helmets for non-invasive ventilation of the known type reveal some drawbacks related to the fact that removal thereof from the head of the patients often requires subjecting the latter to complex and uncomfortable operations, disturbing the patients in question especially if the health conditions thereof are highly critical.

Such drawback is accentuated by the fact that the helmet should be well fitted in the head of the patient and subsequently removed therefrom, not only at the beginning and at the end of the therapy, but also every time there arises the need to gain access to the head of the patient for cleaning operations, routine interventions or extraordinary interventions, for example, in case of emergency.

It can be observed that, especially in case of emergency intervention, the operations of removing the helmet should be extremely prompt.

In order to overcome such drawbacks there is known the use of helmets for non-invasive ventilation of patients whose container bodies are provided, at the front part thereof, with access openings, which are usually hermetically closed by closure elements, such as for example zips or rigid unions.

Should there arise the need for direct intervention to the face of the patient, the personnel may open the closure elements and gain free access to the face of the patient by means of the access opening.

However such helmets reveal some drawbacks two to the fact that both the zip and the union are not always efficient besides the fact that the opening thereof is not always easy and quick to perform for the designated personnel. Furthermore, in order to have comfortable access to the face of the patient the access opening should be necessarily sufficiently wide at least to allow passing the hands of the designated operator to perform the intervention operations or such to allow uncovering the portion of the container body above the opening so as to free the head of the patient.

The required width of the access opening, alongside the fact that the container body is often made of a substantially soft material, amplifies the complexity of the action when opening the closure elements, thus limiting the range of use of such helmets.

Document U.S. Pat. No. 5,819,728 illustrates an example of a helmet of the described type, which is essentially used in oxygen-based therapies used in a hyperbaric chamber.

The helmet described in the aforementioned document comprises a container body in which there can be housed the head of the patient and having a first rigid ring fixed at an open end thereof.

The helmet also comprises a second rigid ring provided with a flexible collar adapted to fasten against neck of the patient.

The first and the second rigid ring are sealingly coupled to each other by means of an annular gasket, of the O-ring type, which is interposed between the outer side of one of the two rings and the inner side of the other ring.

The outer sides of the gasket intervene both for providing sealing against gas leakage from the helmet for securing the two rigid rings together.

Such helmets of the known type, which are exclusively used for hyperbaric oxygen therapy, in which there is present a positive pressure within the hyperbaric chamber, cannot be used for non-invasive ventilation therapy, CPAP, in that the internal positive pressure that the helmet is subjected to, would overcome the retention force of the rings, radially exerted by the gasket, thus opening the helmet.

Even were the pressure of the gases within the helmet unable to overcome the retention force that the gas exerts on the rigid rings, the radial gasket would not guarantee the hermetic sealing of the helmet, where subjected to a positive and high internal pressure.

An object of the present invention is to overcome the previously mentioned drawbacks of the prior art, through a simple, rational and inexpensive solution.

Such objects are attained by the characteristics of the invention indicated in the independent claim. The dependent claims outline preferred and/or particularly advantageous aspects of the invention.

DISCLOSURE OF THE INVENTION

In particular, the invention provides a helmet for non-invasive ventilation of patients comprising:
- a container body in which there can be housed the head of a patient, provided with at least one optically transparent portion for example, an inlet pipe for introducing air, an outlet pipe for releasing used air and an open end to which a first rigid ring is fixed; and
- an elastically yieldable collar which can be sealingly coupled to the neck of the patient and fixed to a second rigid ring which can be sealingly removably associated to said first rigid ring
- an inlet pipe for introducing a breathable gas into the inner volume enclosed by said container body and said collar, and a gas outlet pipe for releasing exhaled gases from said volume.

According to the invention, the helmet comprises bayonet-like coupling means adapted to removably couple the first and the second rigid ring with respect to each other.

Due to this solution, the coupling between the two rigid rings occurs safely and in a manner such to be able to efficiently bear a positive pressure within the helmet, also simultaneously improving the sealing of the helmet.

BRIEF DESCRIPTION OF THE DRAWINGS

Further characteristics and advantages of the invention will be apparent from reading the following description provided by way of non-limiting example, with reference to the figures illustrated in the attached drawings.

FIG. 7 is a top view of the helmet of FIG. 4.

PREFERRED EMBODIMENT OF THE INVENTION

Figure 1:
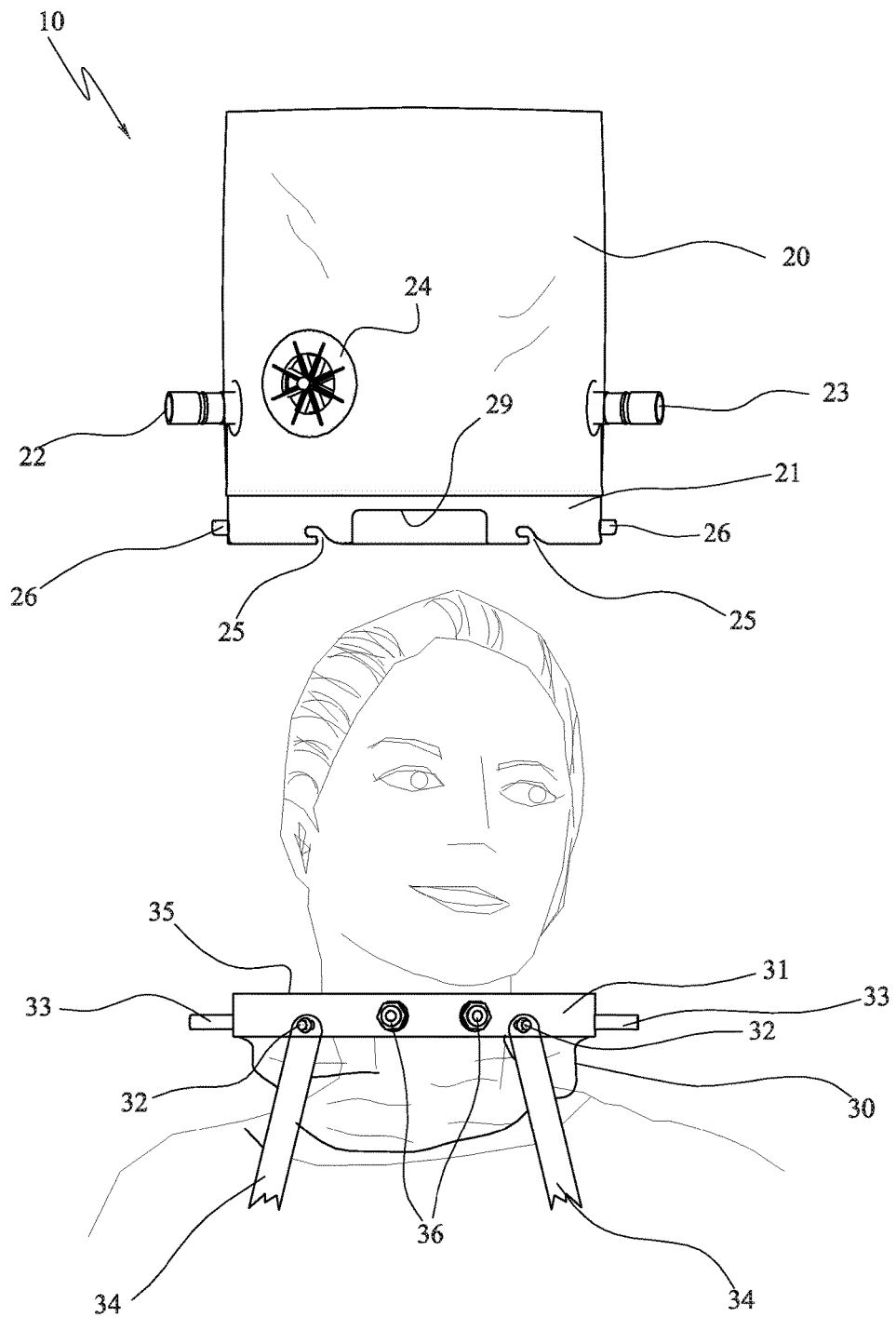
FIG. 1 is an exploded view of a helmet according to the invention, partly worn by a patient.
Figure 2:
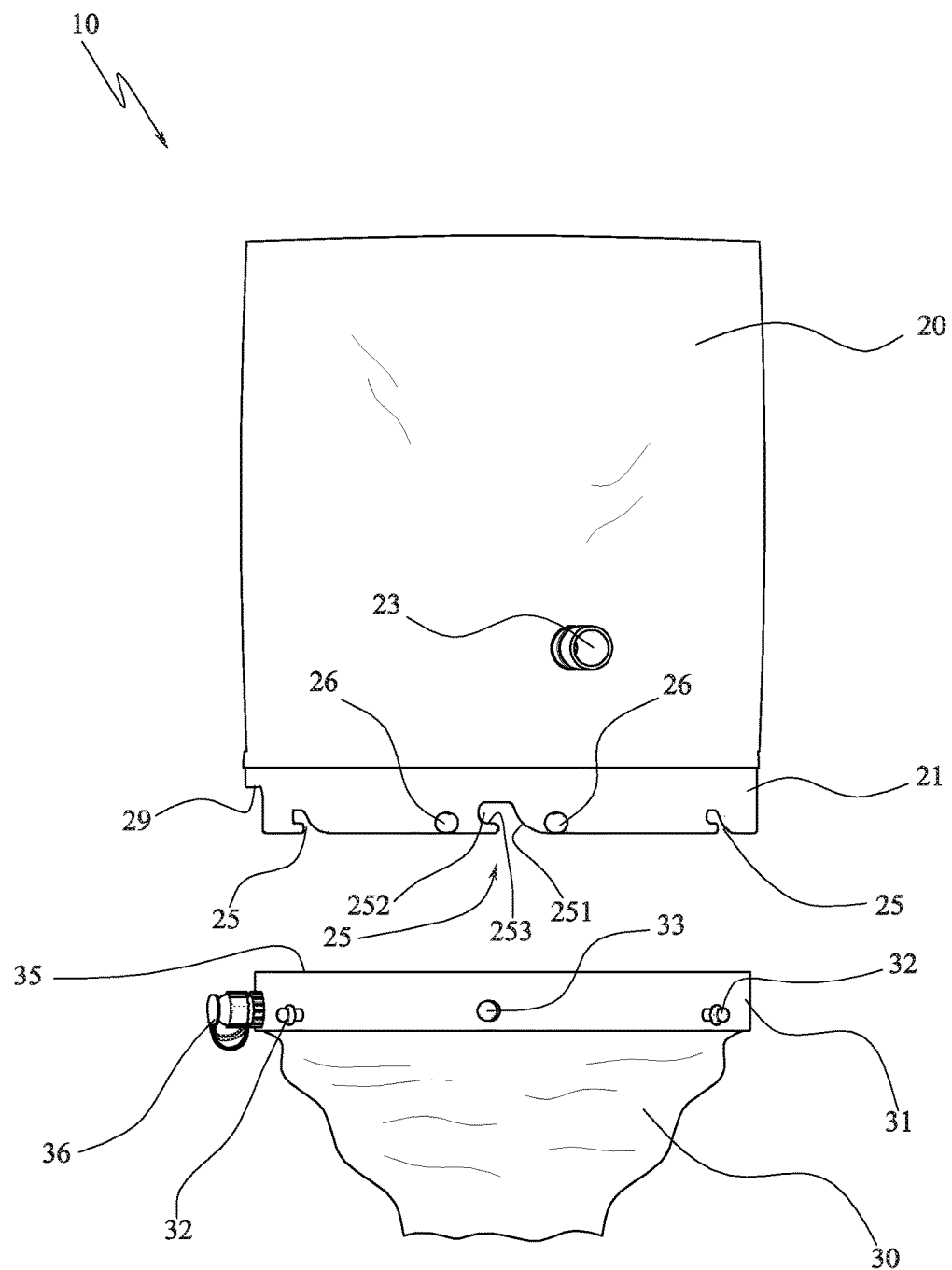
FIG. 2 is an exploded side view of the helmet of FIG. 1 from the left.
Figure 3:
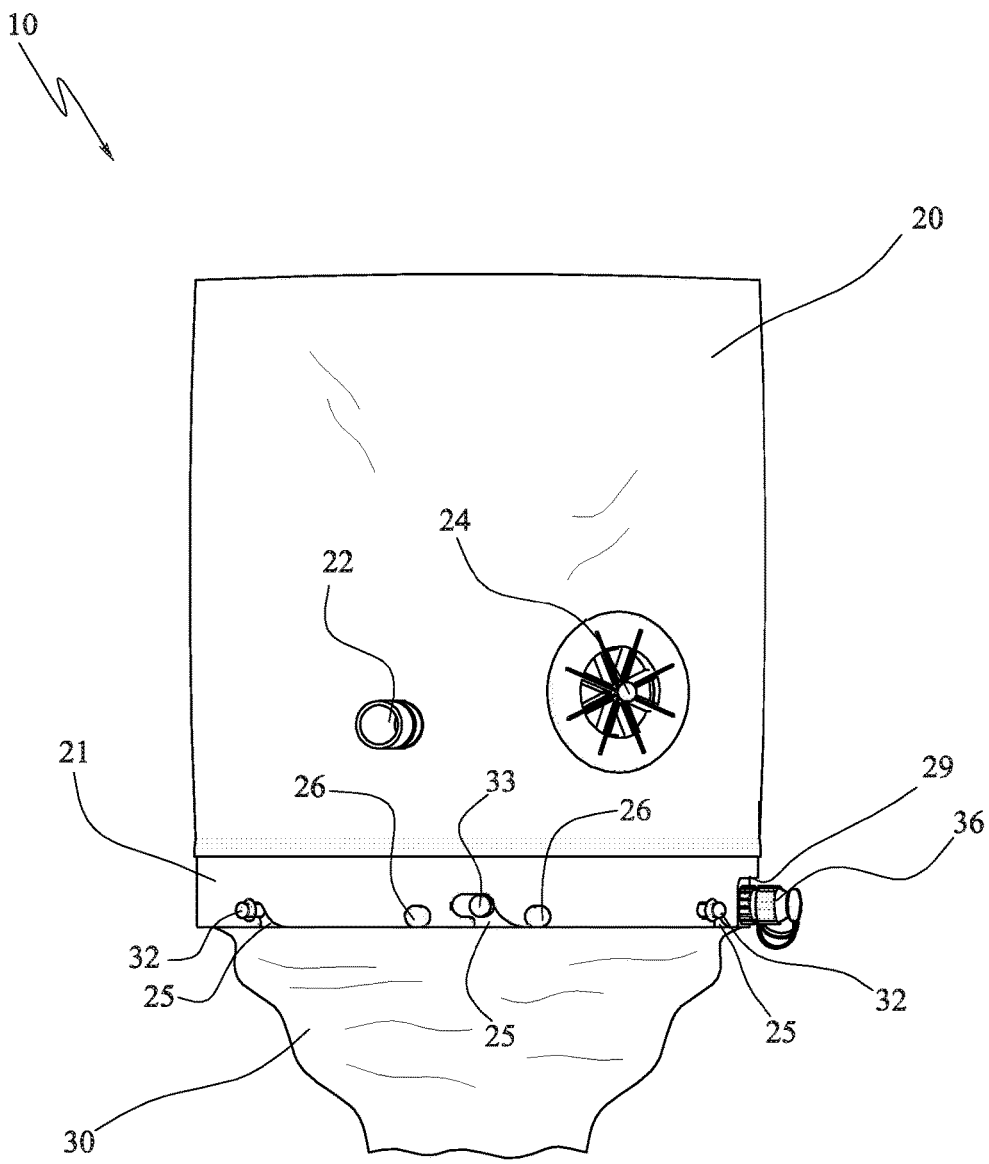
FIG. 3 is an exploded side view of the helmet of FIG. 2 from the right in an intermediate assembly configuration.
Figure 4:
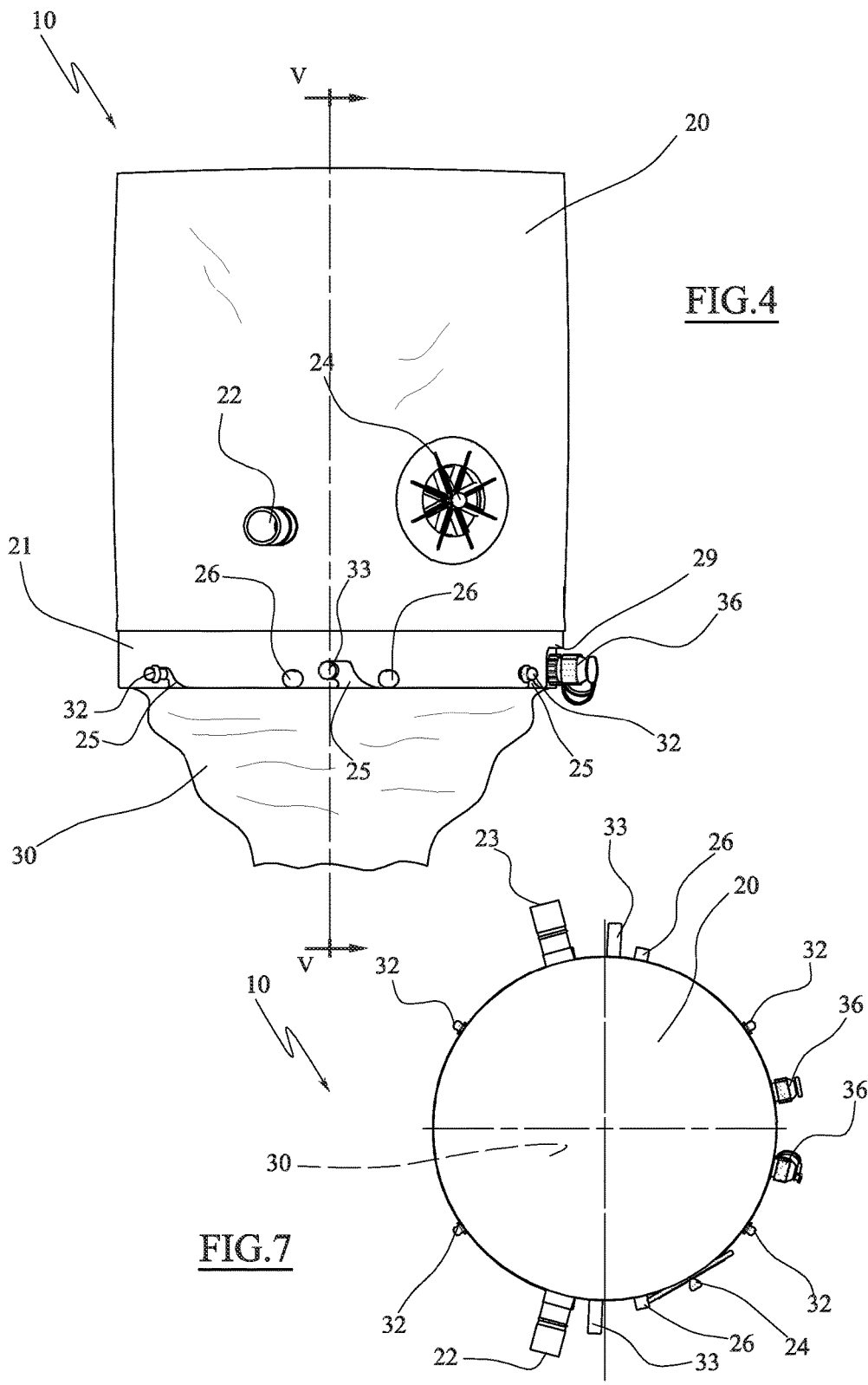
FIG. 4 is a side view of the helmet of FIG. 2 from the right in an assembled configuration.
Figure 5:
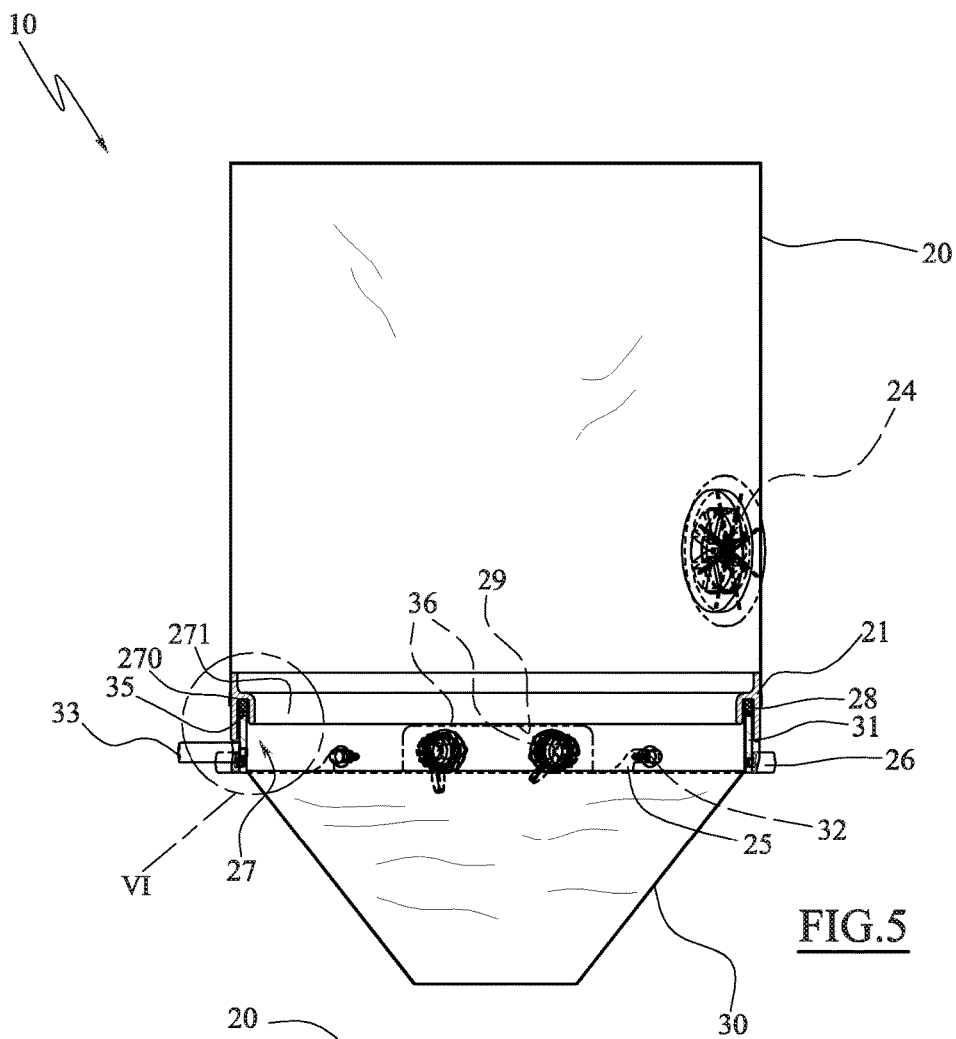
FIG. 5 is the view along the line of section V-V of FIG. 4.

With particular reference to such figures, a helmet for non-invasive ventilation of patients in general is indicated in its entirety with 10.

The helmet 10 comprises a container body 20 which is advantageously made up of a cylindrical element, closed at one end and open at the opposite end, made of optically transparent non-dilatable though flexible material.

The container body 20 at the lower open end thereof is advantageously connected to a first rigid ring 21, through thermo-sealing or any other fixing technique capable of guaranteeing hermetic and stable sealing between the two.

The helmet 10 comprises, moreover, means for introducing air (or mixture of oxygen and air or oxygen) within the internal volume enclosed by the container body 20 and the collar 30 and outflow means of the exhaled gases by the same.

In the example shown, the inlet means comprise an inlet pipe 22 for the introduction of air into the helmet 10 (e.g. a pipe of standard size for the connection to usual pipes for the supply of breathable gas such as air, oxygen or mixtures of oxygen and air), said inlet pipe 22 is, for example, fixed to the container body 20, for example in any part of the same.

The outflow means comprise an outlet pipe 23 of the exhaled gases (e.g. a pipe of standard size for the connection to usual pipes or PEEP valves or other devices suitable to allow the outflow of the exhaled gases); for example said outlet pipe 23 is fixed to the container body 20, for example, in any part of the same.

Alternatively, the inlet pipe 22 and/or the outlet pipe 23 can be fixed to the helmet 10 elsewhere, for example in correspondence of the rigid rings 21,31 or of the collar 30, depending on the needs. Furthermore, the container body 20 can be provided with possible closable openings for access thereinto and so on and so forth and with an anti-suffocation valve 24, i.e. a two-directional valve that is capable of placing the external of the container body 20 in communication with the internal thereof.

Some embodiments of the helmet may provide for that the container body 20 be provided with openings that can be closed by means of a zip (or any other means) to provide a further access to the patient.

The helmet 10 also comprises a collar 30 which is, advantageously, made of elastically yieldable material to be sealingly coupled to the neck of the patient, which is connected to a second rigid ring 31, for example by means of fixing techniques capable of guaranteeing hermetic sealing between the collar 30 and the second rigid ring 31.

The second rigid ring 31, which for example is coated with soft material, can be sealingly removably associated to the first rigid ring 21 (also for example coated with soft material), as more apparent in the description that follows.

The helmet 10 comprises bayonet-like coupling means adapted to removably couple—with respect to each other—the first and the second rigid ring, respectively 21 and 31.

The bayonet-like coupling means comprise two coupling elements 25 and 32 which are associated, respectively, to the first rigid ring 21 and to the second rigid ring 31.

The coupling elements, in particular, comprise a plurality of pins 32, for example fixed to a lateral surface of the second rigid ring 31, and a respective plurality of housing seats 25, for example obtained in the first rigid ring 21. In practice, each pin 32 is adapted to be removably inserted into a housing seat 25 following a slight mutual rotation between the first and the second rigid ring with respect to the mutual approaching axis.

In the embodiment shown in the figures, the second rigid ring 31 is adapted to be substantially fittingly inserted into the first rigid ring 21, coaxially; the bayonet-like coupling means comprise a plurality of pins 32, which project radially from the external lateral surface of the second rigid ring 31 and they are substantially equally spaced from each other, and a corresponding plurality of housing seats 25, obtained in the first rigid ring 21 and also equally spaced from each other.

Each housing seat 25 is substantially configured to form an extended slot (substantially L-shaped) which defines a first open section 251, at the lower edge of the first rigid ring 21, adapted to allow the access of the pin 32.

The first section 251 has an inclination with main direction parallel to the mutual approaching axis (vertical in the figure).

Each housing seat also comprises a second section 252, consecutive to the first, which is inclined with main tangential direction (horizontal in the figure).

The second section 252 has a width transverse to the sliding direction of the pin 32 substantially equivalent to the width of the pin 32, so that the latter can slide substantially at contact with the walls of the second section 252.

Each second section defines an engagement portion 253 (the lower wall of the second section or both walls of the second section), for example concave (with concavity facing towards the internal of the container body 20) or rectilinear, in which there can be stably housed one of the pins 32 when the helmet 10 is in configured assembly, i.e. when the two rigid rings 21 and 31 are stably coupled to each other.

At least two pins 33 of the plurality of pins 32—which are arranged substantially diametrically opposite with respect to each other and are adapted to be positioned laterally on the patient, once the helmet 10 is worn by the patient—have a free end configured to be gripped, having for example an ergonomic shape.

Pegs 26, also adapted to be gripped, are provided on the sides of the housing seat 25 which houses such pins 33 which can be gripped. The mutual rotation of the two rigid rings 21 and 31 occurs by mutually approaching or moving the pins 33 and the pegs 26 apart (in one or the other direction of rotation) obtained using only two fingers of the hands of the operator.

For the sake of exhaustive description it should be observed that the helmet 10 is provided with a pair of harnesses 34 which are of the armpit type and which are engaged with some of the pins 32 (not the pins 33 and adapted to be arranged at a front and rear position once the patient wears the helmet) and which, advantageously, are coated with soft anti-decubital material with antibacterial treatment; such harnesses have the function of preventing the helmet 10 from raising two to the positive pressure therein.

Alternatively, as illustrated in the second embodiment of the helmet 10 shown in FIGS. 8-11, the helmet 10 comprises a bearing 40, which can be inflated by means of an outer port 41, which has a portion 42 fixed or welded to the second rigid ring 30, so that—during use—it remains arranged externally with respect to the collar 30, in practice being arranged around the neck of the patient beneath the collar.

The bearing 40 is substantially doughnut-shaped and it has an open sector 43 adapted to facilitate the insertion thereof on the neck of the patient which, during use, is such to be substantially arranged below the chin of the patient. Furthermore, the bearing 40 has at least one pair of ears 44, which are arranged substantially on the opposite side with respect to the portion 42 and they are provided with through slots 45 adapted to be inserted in respective two pins 32, so as to be able to be removably coupled to the second rigid ring 31 and be arranged substantially coaxial therewith.

Furthermore, the helmet 10 comprises an annular base 50 which is made up of two semicircles 501 and 502 mutually connected to an end by hinging means which comprise a hinging pin 51 and which, at the other end have joining means which comprise a tab 52 arranged on one of the two semicircles and which can be inserted into a slit 53 arranged in the faced end of the other semicircle.

The annular base 50 may be obtained by means of elements that are substantially rigid or which have a given flexibility and which are obtained by means of a relatively thin panel made of plastic material, for example, of the polyvinyl chloride, polypropylene, acrylonitrile-butadiene-styrene, polyoxymethylene type, known in the market under the commercial name of Delrin or other polymers.

The annular base 50 is provided with fixing means adapted to fix the same to the second rigid ring 31.

In practice, from the annular base 50 there departs a plurality of radial tabs 54 fixed, welded or made in a single piece with the annular base, which have a through hole 55 for providing a stable and removable connection with some of the pins 32 (for example, not the pins 33 and adapted to be arranged in a front and rear position once the patient wears the helmet).

When the annular base 50 is stably connected to the second rigid ring 31, the collar 30 is made to abut on the annular base 50 and be compressed therein by the positive pressure present within the helmet 10.

Furthermore, the annular base 50 comprises an external edge 56 folded upwards adapted to be substantially fittingly inserted on the first and second rigid ring 21 and 31, when the helmet 10 is in assembled configuration.

Thus, the annular base 50 defines an abutment plane for the collar 30 which, somehow, stiffens the structure strongly hindering or limiting the elastic deformation thereof.

This allows preventing the helmet 10, due to the breathing of the patient, from oscillating vertically due to the excessive elasticity of the collar 30.

In practice, the presence of the annular base 50 allows strongly limiting the variation of the internal volume of the helmet 10, which is normally due to the flexibility of the flexible collar 30, which—as known—causes a non-synchronism between the beginning of the spontaneous breathing action of the patient and the response of the fan which is provided for insufflating air/oxygen.

As a matter of fact, the annular base 50 actually lies beneath the chin of the patient, once the collar 30 is sealingly arranged around the neck of the patient and the head of the patient is arranged within the container body 20.

Advantageously, the internal diameter of the annular base 50 is substantially equivalent to or slightly greater than the diameter of the neck of the patient to which the helmet is associated 10, or at least substantially considerably smaller than the maximum diameter of the head of the patient, in that such annular body, once fixed beneath the container body 20, serves as an abutment against the raising of the helmet 10 that would occur when pressurised air/oxygen is insufflated thereinto, simultaneously maintaining the volume inside the helmet substantially constant even during the breathing action.

Advantageously, the aforementioned bearing 40 is adapted to be interposed between the collar 30 and the annular base 50, before the latter is fixed to the second rigid ring 31 as described above.

In practice, the collar 30 directly abuts on the bearing 40 and the abutment plane provided by the annular base 50 supports the bearing.

The collar 30 is in practice held between the bearing 40 and the annular base 50, thus exerting an optimal sealing on the neck of the patient but without having the elastic deformation which negatively impacts the pressure values during the breathing action.

Besides this, due to such solution the helmet 10 can be associated to the patient without requiring harnesses which prevent the lifting thereof with indisputable advantages in terms of the patient's comfort.

Figure 6:
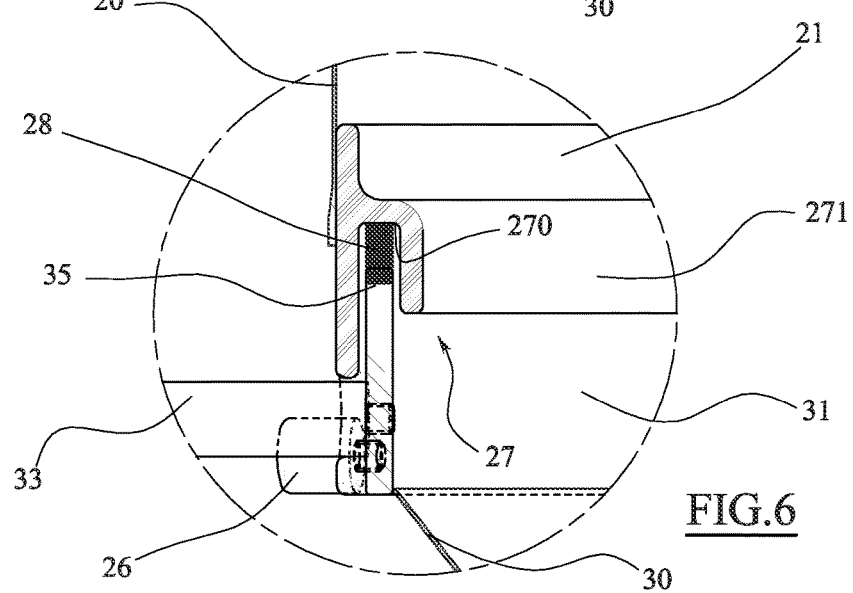
FIG. 6 is an enlargement of the detail VI of FIG. 5.
Figure 8:
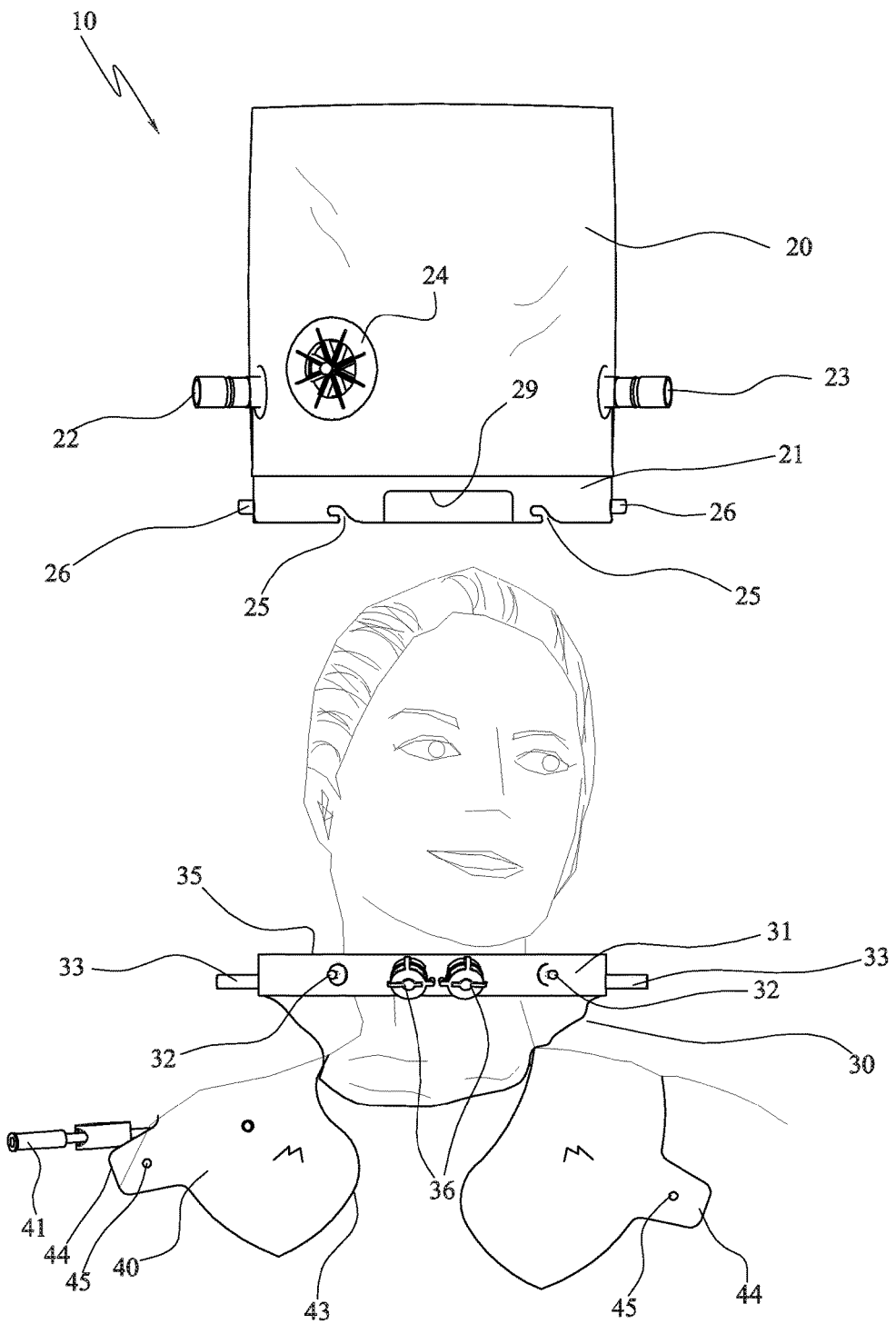
FIG. 8 is an exploded axonometric view of a second embodiment of a helmet according to the invention, partly worn by a patient.
Figure 9:
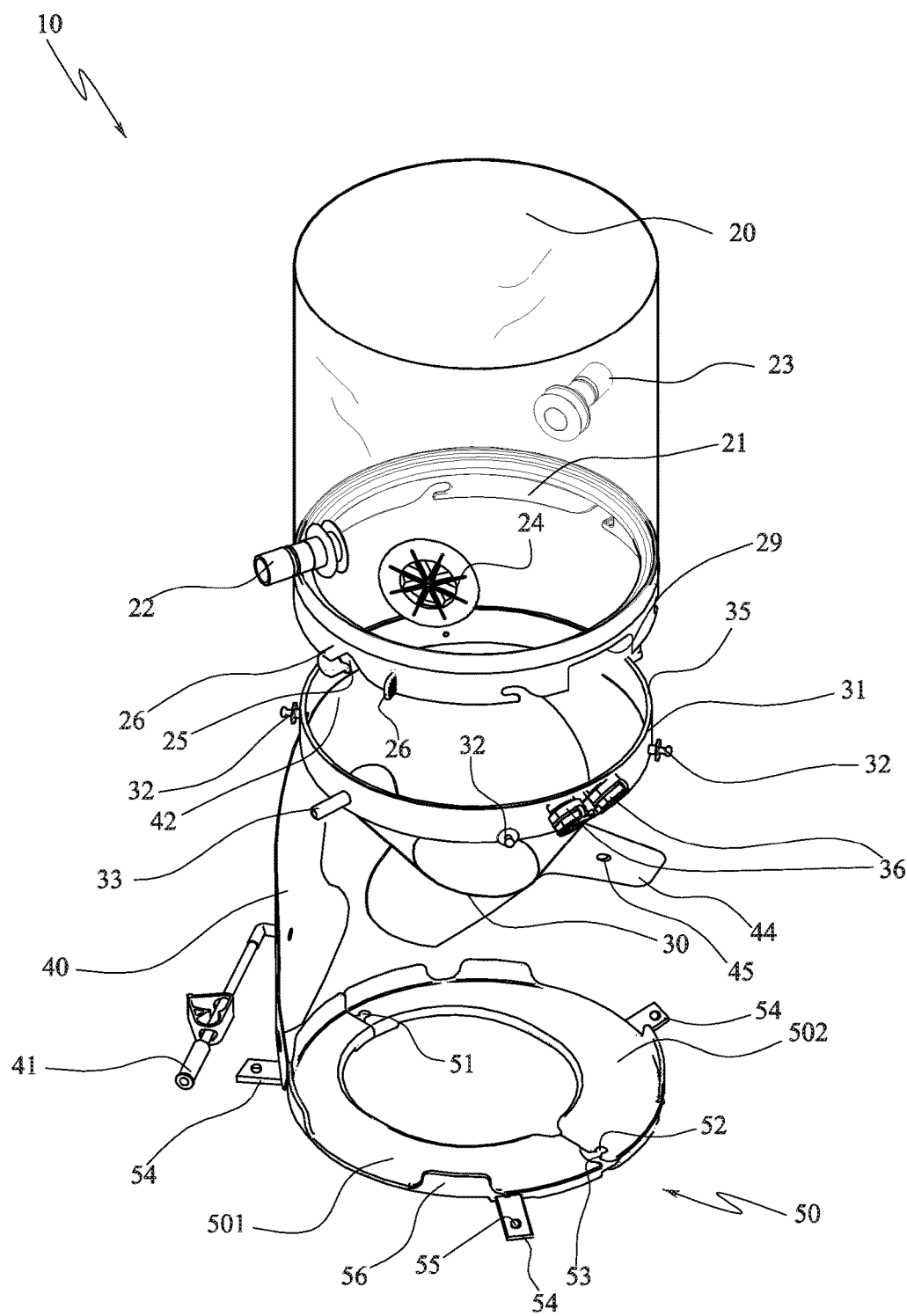
FIG. 9 is an exploded axonometric view of the helmet of FIG. 8.
Figure 10:
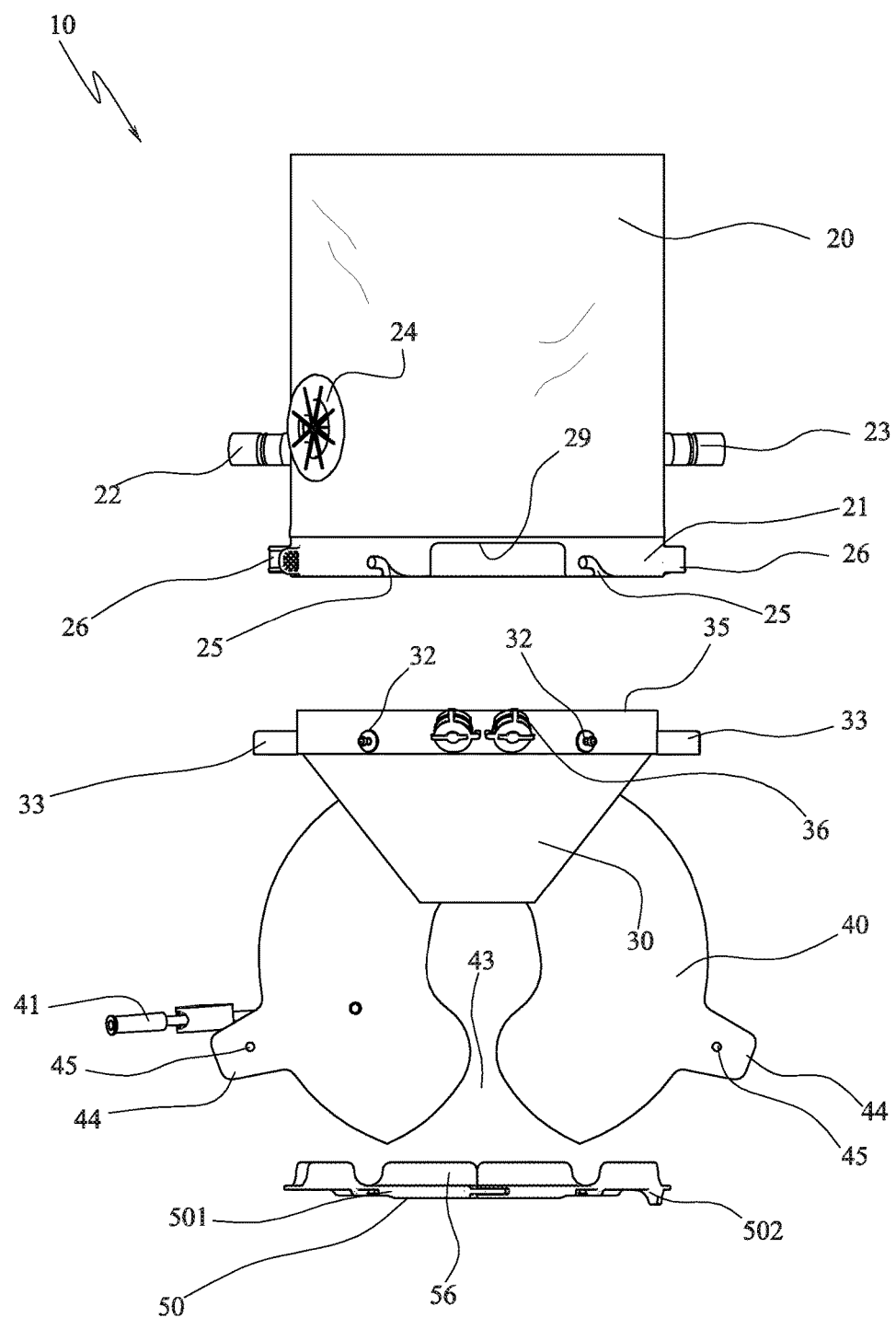
FIG. 10 is a front view of FIG. 9.
Figure 11:
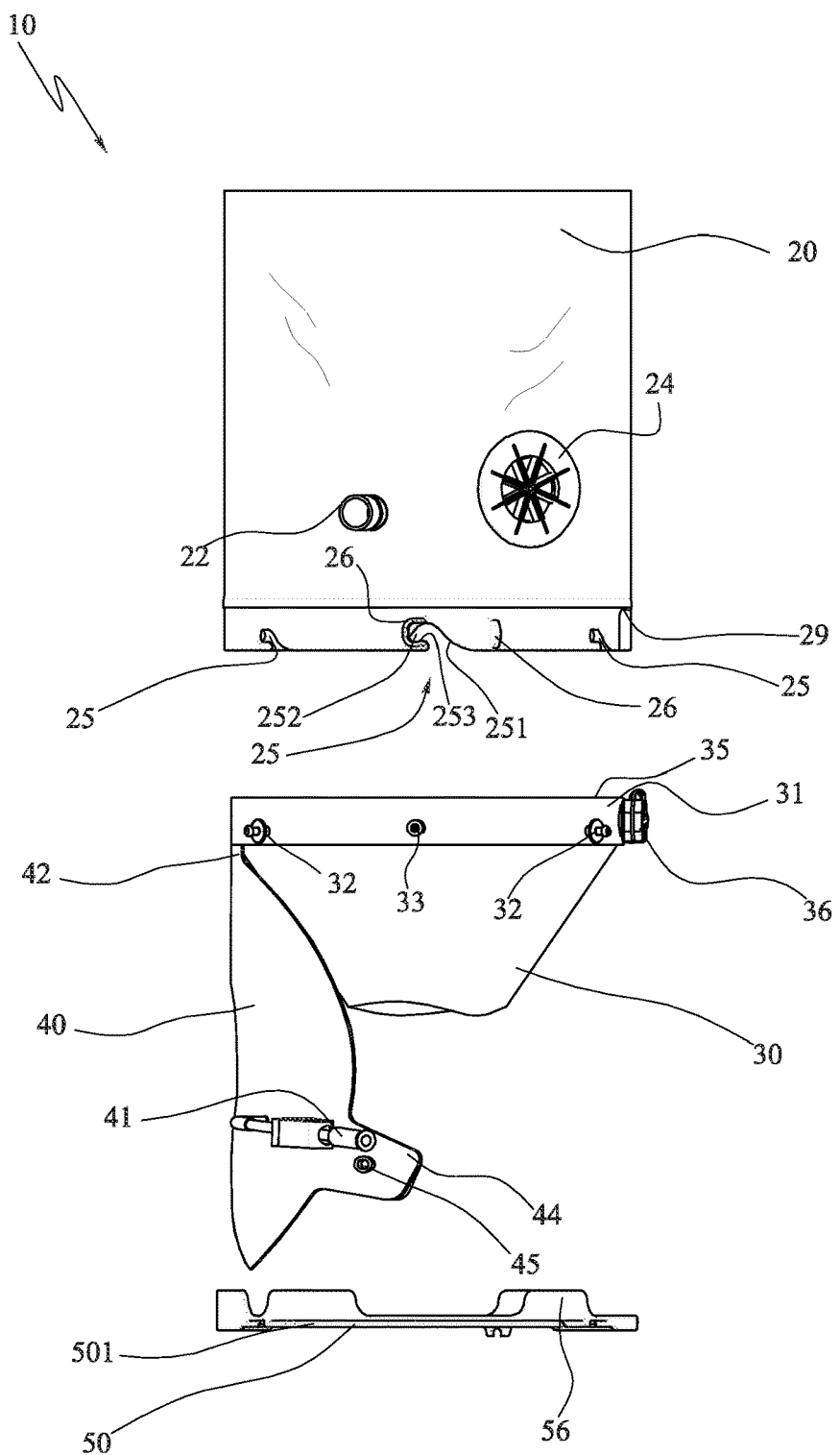
FIG. 11 is a side view of FIG. 10 from the left.

One between the first and the second rigid ring, respectively 21 and 31, comprises an annular seat 27 adapted to house an annular gasket 28, observable in the sectioned detail of FIG. 6.

The annular seat 27, in this case, has a substantially U-shaped transverse section, with concavity facing along the mutual approaching axis, and it is axially accessible.

In the represented example, the annular seat 27 is obtained at the inner lateral surface of the first rigid ring 21 and it is contoured, on one side, by the internal wall of the first rigid ring and, at the upper part and on the other side, by a strip 271 obtained in a single piece with the first rigid ring 21 and folded to form a U-shape on the rigid ring.

The annular seat 27, particularly, has a concavity facing towards the external of the container body 20 (downwards in the figure), so that it can be accessible for the insertion of the annular gasket 28 in the axial direction and from the bottom.

The annular seat 27 is obtained in proximity of the upper edge of the first rigid ring 21, while the coupling means are obtained in proximity of the lower edge of the first and the second rigid ring 21 and 31.

The annular gasket 28 is adapted to be compressed, in use, in the axial direction between the bottom 270 of the annular seat 27 and the upper edge 35 of the second rigid ring 31.

In practice the annular seat 27, is accessible in the axial direction from the bottom even by the second rigid ring 31, whose upper edge 35 is adapted to come to contact—along the entire circumferential development of the upper edge—with the exposed surface of the annular gasket 28 and press it towards the bottom 270 of the annular seat 27.

Such forced contact in the axial direction between the upper edge 35 and the annular gasket 28 allows the sealing connection between the first and the second rigid ring, respectively 21 and 31, and thus the sealing of the entire helmet 10, once worn and assembled.

The annular gasket 28 has at least one exposed surface layer (opposite to the contact one with the bottom 270 of the annular seat 27) made of a material having a low coefficient of sliding friction, for example made of closed cell polyurethane rubber.

In this manner, the upper edge 35 of the second rigid ring 31, which is substantially fittingly inserted into the annular seat 27 following an axial translation along the direction of mutual approach between the first and the second rigid ring 31, can slide without considerable friction on the annular gasket 28 following the low rotation between the two rigid rings 21 and 31 which allows the mutual coupling thereof.

Furthermore, the bayonet-like coupling means are configured so as to keep the annular gasket 28 compressed between the upper edge 35 and the bottom 270 of the annular seat 27 when the helmet is assembled.

In practice, the first section 251 of each housing seat 25 has a length such to allow each pin 32 an axial travel such that the upper edge 35 can slightly compress the annular gasket 28 to the axial end stop.

Furthermore, the engagement portion 253 of the second section 252 of each housing seat 25 (which, for example, can be slightly concave, parallel to the lower edge of the first rigid ring 21 or rising with respect thereto) is arranged at a distance from the lower edge of the first rigid ring 21 such to maintain a give compression of the annular gasket 28 even following the mutual rotation (for coupling) between the two rigid rings 21 and 31.

The sealing between the first and the second rigid ring, respectively 21 and 31, is further accentuated by the fact that such rigid rings are coated, as mentioned, by a soft material, for example rubber or any other material having a given resilience, such to be slightly compressed against the annular gasket 28 (in the respective areas of contact therewith) two to the action of the bayonet-like coupling means.

The second rigid ring 31 comprises through holes to which there are associated connection fittings 36, for example of the fairlead type or any other connection for various instruments suitable for the therapy of the patient, which connect the environment outside the container body 20 with the environment inside the container body 20.

The first rigid ring 21 also has one or more notches 29, open at the lower edge of the rigid ring 21, which are adapted to be radially superimposed on the through holes supporting the connection fittings 36 when the helmet 10 is assembled; in practice the notches 29 provide an opening (arranged externally with respect to the sealed environment the helmet 10) which connects a portion of the second rigid ring 31 with the external (when the helmet 10 is assembled), otherwise the second rigid ring 31 would be completely concealed from the first rigid ring 21 which fits radially superimposed thereon.

Alternatively, connection fittings 36 can be fixedly connected to the collar 30. In the light of what has been described above, the helmet 10 operates as follows.

In order to subject the patient to a non-invasive ventilation therapy it is sufficient that the patient primarily wears the collar 30, ensuring that it adheres to the neck.

In this configuration, the helmet 10 is open and the head of the patient is accessible from all walls thereof.

The helmet 10 is closed by simply fitting the head of the patient into the container body 20, by approaching—through axial translation—the first rigid ring 21 to the second rigid ring 31.

Upon aligning the pins 32 of the second rigid ring 31 to the first sections 251 of the first rigid ring 21, for example by actuating—using the thumb and index finger of each hand—the pins 33 and one of the pegs 26, there follows the actuation of the two rigid rings 21 and 31 mutually approached through a slight axial translation (which partly superimposes the two rigid rings), wherein the pins 32 slide into the first section 251; at the end of the first section 251—through the rotation of the rigid rings 21 and 31 according to a slight mutual rotation—the pins 32 may slide along the second section 252.

The bayonet coupling, as mentioned, allows the annular gasket 28 to be compressed between the annular seat 27 and the upper edge 35 of the second rigid ring 31, so that the helmet 10 is substantially closed sealingly.

In such configuration, the helmet 10 is stably closed, also two to the fact that pressurized air which generates—in the helmet—a positive pressure which presses the pins 32 against the engagement portion 253 is insufflated through an inlet pipe 22.

Furthermore, such bayonet-like coupling means allow a prompt opening intervention of the helmet 10, in that by simply rotating the pins 33 and the other peg of the pair of pegs 26 using the thumb and index finger of each hand in the direction opposite to the one that caused the coupling, the pins 32 traverse the second section 252 backwards and, upon entering the first section 251, they are free to slide therealong (for example under the thrust of the positive pressure inside the helmet), so that the first rigid ring 21 slips off the second rigid ring 31 and the container body 20 can be removed from the head of the patient, leaving the collar 30 in place.

The invention thus conceived can be subjected to numerous modifications and variants all falling within the inventive concept. Furthermore, all details can be replaced by other technically equivalent elements.

In practice the materials used, as well as the contingent dimensions, may vary depending on the requirements without departing from the scope of protection of the claims that follow.

The invention claimed is:

1. Helmet (10) for non-invasive ventilation of patients comprising:
   a container body (20) in which there can be housed the head of a patient, wherein the container body (20) is provided with at least one optically transparent portion having an open end with a first rigid ring (21) fixedly fixed to the open end of the optically transparent portion;
   an elastically yieldable collar (30) which can be sealingly coupled to the neck of the patient, wherein the elastically yieldable collar (30) is fixedly fixed to a second rigid ring (31) which can be sealingly removably associated to said first rigid ring (21),
   an inlet pipe (22) for introducing a breathable gas into the inner volume enclosed by said container body (20) and said collar (30), and a gas outlet pipe (23) for releasing exhaled gases from said inner volume,
   bayonet-like coupling means adapted to removably couple the first and the second rigid ring with respect to each other (21,31) wherein the bayonet-like coupling means comprise two coupling elements (32, 25) respectively associated to the second rigid ring (31) and to the first rigid ring (21), the two coupling elements (32, 25) including: a plurality of pins (32,33), fixed to the second rigid ring (31) of the collar (30), and respective housing seats (25), obtained in the first rigid ring (21)

of the container body (20), adapted to provide a mutual coupling following a slight mutual rotation between the first and the second rigid ring (21,31) with respect to the mutual approaching axis, wherein the helmet further comprises:
- pegs (26) fixed to the first rigid ring (21) and provided on sides of the housing seats (25) and suitable to be gripped together with the pins (32, 33) of the second ring (21), when the pins (32, 33) are coupled with the respective housing seat (25), of the first rigid ring (21), in such a way to rotate the pins (32, 33) relative to respective housing seat (25) to facilitate the removal of the first rigid ring (21) from the second ring (31), and
- a device for preventing the helmet (10) from rising due to the positive pressure therein, wherein the device is engaged with some of the pins (32) of the second rigid ring (31) in order to allow the removal of the first rigid ring (21) and the container body (20) fixed thereto from the collar second rigid ring (31), leaving the collar (30) and the collar second rigid ring (31) in place around the patient's neck.

2. Helmet (10) according to claim 1, wherein each housing seat (25) comprises an extended slot defining a first open access section (251) inclined with main direction parallel to the mutual approaching axis and a second section (252) inclined with main tangential direction.

3. Helmet (10) according to claim 2, wherein each second section (252) defines an engagement portion (253) in which one of said pins (32) can be stably housed.

4. Helmet (10) according to claim 1, wherein at least one between the first (21) and the second (31) sealing ring comprises an annular seat (27) adapted to house an annular gasket (28), said annular seat (27) having a substantially U-shaped transverse section with concavity facing along the mutual approaching axis and being axially accessible; the annular gasket (28) being adapted to be compressed, in use, in the axial direction between the bottom (270) of the annular seat (27) and the upper edge (35) of the other between the second (31) and the first (21) rigid ring.

5. Helmet (10) according to claim 4, wherein said gasket (28) has at least one surface layer made of a material having a low coefficient of sliding friction.

6. Helmet (10) according to claim 5, wherein the gasket (28) is made of closed cell polyurethane rubber.

7. Helmet (10) according to claim 6, wherein the second rigid ring (31) comprises through holes to which there are associated connection fittings (36) between the environment outside and the environment inside the container body (20), the first rigid ring (21) having a notch (29) adapted to be radially superimposed on said through holes when the helmet (10) is assembled.

8. Helmet (10) according to claim 4, wherein the second rigid ring (31) is adapted to be substantially fittingly inserted into the first rigid ring (21), the upper edge (35) of the second rigid ring (31) being adapted to be inserted into the annular seat (27) obtained at the inner surface of the first rigid ring (21), following the mutual approaching translation between the first rigid ring and the second rigid ring.

9. Helmet (10) according to claim 4, wherein the bayonet-like coupling means are configured so as to keep the gasket (28) compressed between the upper edge (35) and the bottom (270) of the annular seat (27) when the helmet (10) is assembled.

10. The helmet (10) according to claim 1, wherein each pin (32, 33) radially projects from an external lateral surface of the second rigid ring (31).

* * * * *